United States Patent [19]
Brigham

[11] Patent Number: 5,305,876
[45] Date of Patent: Apr. 26, 1994

[54] ORTHODONTIC BAND STERILIZATION CASSETTE

[76] Inventor: Susan K. Brigham, 7324 E. Ironwood Ct., Scottsdale, Ariz. 85258

[21] Appl. No.: 121,698

[22] Filed: Sep. 15, 1993

Related U.S. Application Data

[63] Continuation-in-part of Ser. No. 33,290, Mar. 16, 1993, abandoned, which is a continuation of Ser. No. 811,657, Dec. 23, 1991, abandoned.

[51] Int. Cl.⁵ .......................... A61L 2/00; B65D 81/00
[52] U.S. Cl. ................. 206/63.5; 206/459.5; 422/297; 422/300
[58] Field of Search .................. 206/63.5, 363–370, 206/438, 439, 459.5; 422/297, 300, 310

[56] References Cited

U.S. PATENT DOCUMENTS

| | | | |
|---|---|---|---|
| 2,701,635 | 2/1955 | Mills | 206/73 |
| 2,739,734 | 3/1956 | Pugh | 220/83 |
| 3,092,443 | 6/1963 | Dietz | 206/350 |
| 4,333,567 | 6/1982 | Leonard | 206/368 |
| 4,402,407 | 9/1983 | Maly | 206/438 |
| 4,854,475 | 8/1989 | Riihimaki | 220/337 |
| 4,898,276 | 2/1990 | Georgakis | 206/369 |
| 4,959,199 | 9/1990 | Brewer | 422/300 |
| 4,978,510 | 12/1990 | Smith | 422/310 |
| 5,022,858 | 6/1991 | Castellini | 433/97 |
| 5,084,251 | 1/1992 | Thomas | 422/300 |
| 5,131,532 | 7/1992 | Ives | 422/300 |

FOREIGN PATENT DOCUMENTS 0306311  2/1929  United Kingdom ............... 220/345

Primary Examiner—Jimmy G. Foster
Attorney, Agent, or Firm—Donald J. Lisa

[57] ABSTRACT

A multiple compartment box for use in sterilizing and segregating small parts, such as orthodontic bands. The box is shaped as a cassette and is divided into a plurality of small compartments by a plurality of dividers, which include at least one intersecting divider mutually perpendicular to the other dividers. The entire cassette including dividers and lid is preferably made of a material which is resistant to repeated sterilization processing, such as, a metal. Each compartment is identified with respect to an orthodontic band associated with a particular jaw, quadrant and tooth of a patient's mouth to assist is segregating and differentiating the band. The dividers have substantially flat edges which closely abut the inner adjoining surfaces of the sidewalls, endwalls, base and lid to prevent passage of bands identified for one compartment to another compartment. The box incorporates a sliding lid which can be opened or closed without interfering with the divider edges or the contents of the compartments.

20 Claims, 1 Drawing Sheet

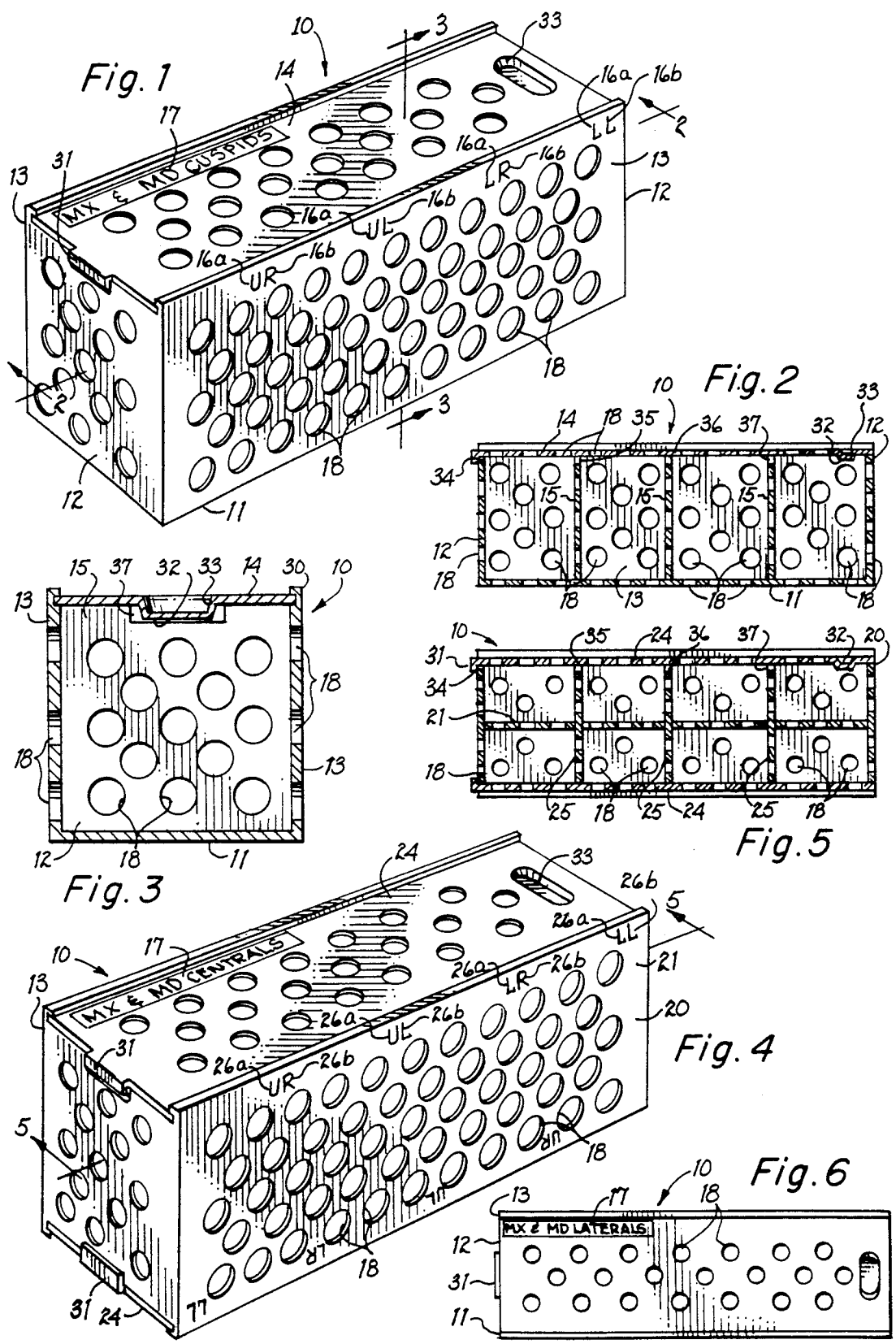

ORTHODONTIC BAND STERILIZATION CASSETTE

RELATED APPLICATION

This is a continuation-in-part of copending application Ser. No. 08/033,290 filed on Mar. 16, 1993 now abandoned, which is a continuation application of Ser. No. 07/811,657 filed Dec. 23, 1991, now abandoned.

BACKGROUND OF INVENTION

The invention relates to the field of sterilization devices. It further relates to cassettes used to hold small parts to prevent their loss or damage during the sterilization is process.

It is a common problem in the fitting of orthodontic bands that many of the bands are lost or damaged during the fitting, cleaning or sterilizing process. A further problem is the large number of orthodontic bands. There are 32 different sized bands for each of 28 teeth, making a total of 896 different sized bands. In fitting orthodontic bands it is frequently necessary to try numerous variously sized orthodontic bands until the appropriately sized band is found for a particular tooth. Each band which is attempted and not appropriately sized is removed from the mouth and then placed on a counter until the fitting process is completed. After the fitting is completed it is necessary for the orthodontist or an assistant to collect the unused bands, wash them by hand and then collect the bands and sterilize them. Due to the small size of the bands, they are easily dropped or mishandled which can cause them to be lost or damaged. Further, after the bands are removed from sterilization, they must be sorted by hand, and replaced in the appropriate containers for the next use. This sorting requires a great deal of time and effort.

The placement of the orthodontic bands on a counter after they have been removed from a patients mouth increases the possibility that the orthodontist or his or her assistants may come into contact with the bands which are exposed to oral fluids. This increases the risk to the orthodontist or assistants of exposure to germs or disease.

Many type of cassettes or boxes are known for use in sterilizing equipment used in a medical or dental setting. Examples of these inventions are shown in the Brewer patent, U.S. Pat. No. 4,959,199 which discloses a cassette used for the sterilization of dental instruments; the Riihimaki et al patent, U.S. Pat. No. 4,854,475 which discloses a cassette for sterilizing dental instruments; the Maly patent U.S. Pat. No. 4,402,407 which discloses a surgeon's chest for sterilizing surgical instruments; and the Dietz patent U.S. Pat. No. 3,092,443 which discloses a dental burr holder and sterilizer.

The art also discloses boxes for storage of small parts such as orthodontic brackets as shown by the Georgakis patent, U.S. Pat. No. 4,898,276.

The problem in the art is that most of the sterilization devices are designed for the sterilization of dental instruments which are of a sufficient size that there is little risk of these items being lost in the sterilization process. Further dental and surgical instruments are of sufficient size and strength so that they are not likely to be damaged during the handling or processing necessary in the sterilization phase. There is not known a cassette manufactured of sufficient materials to readily withstand repeated use in the dental sterilization process and which can be used to hold small parts, such as orthodontic bands and that can assist in the segregation and organization of these parts.

Another problem with the current method of sterilizing orthodontic bands is that they are often placed in standard autoclave bags for sterilization. These bags are disposed of after each use which causes a repeated expense.

SUMMARY OF THE INVENTION

The present invention is a sterilization cassette which includes two generally parallel sidewalls and two generally parallel endwalls generally perpendicular to the sidewalls, the sidewalls and endwalls being attached to a base also generally perpendicular to the sidewalls, the sidewalls, endwalls and base defining a generally rectangular container having an upper opening adjacent an upper edge of the sidewalls and endwalls. The cassette has a plurality of a first set of dividing wall members supported in the container, each having end, top and bottom edges, which thereby define a plurality of discrete compartments within the rectangular container. Also included is a generally flat lid portion operably associated with the upper edge of the side or end walls to releaseably close the upper opening. Each of the compartments is labelled with a first indicia identifying a jaw of a patient's mouth and a second indicia identifying a quadrant of a patient's mouth. A third indicia is disposed on the container or lid identifying each of the discrete compartments with respect to an associated orthodontic band for a tooth. The cassette has a plurality of openings in the container or lid for admitting a sterilization liquid to each compartment for sterilizing orthodontic bands placed therein. Each of the divider edges are closely abutting its associated adjacent inner surface of the base, wall and lid, respectively, and are sufficiently flat to prevent passage therebetween of an orthodontic band identified for one compartment to an adjacent compartment.

A further feature of the invention is a slidable lid which includes an inner groove at an upper edge of each sidewall with a generally flat lid portion engaging and reciprocable within the grooves to open and close the container without interference with the top edges of the dividing wall members or the contents of the compartments.

A still further feature of the invention is that the entire cassette and all dividing wall members may be made of metal, such as, stainless steel, that can withstand repeated sterilization processing.

Another feature of the invention is that the first set of dividing wall members are generally parallel to the endwalls of the cassette and are each generally perpendicularly intersected by, or interlocking with, at least one of a second set of dividing wall members which is generally parallel to the sidewalls thereby further dividing the cassette into discrete compartments.

It is an object of the invention to provide a cassette which prevents or minimizes the loss or damage to orthodontic bands occurring during the fitting and sterilization process.

It is a further object of the invention to provide a cassette which allows for the segregation of orthodontic bands during the fitting process by dividing the cassette into a plurality of easily accessible discrete compartments each of which is identified to particular bands which are prevented from passing to other compartments during the sterilization process.

It is a further object of the invention to provide a sterilization cassette which reduces the time spent sorting orthodontic band or other small parts after sterilization.

It is a further object of the invention to provide a cassette which assists in maintaining a clean and sterile environment in an orthodontic or dental office during the procedure of fitting orthodontic bands.

It is a further object of the invention to provide a reusable sterilization cassette which reduces the cost of sterilizing orthodontic bands.

BRIEF DESCRIPTION OF THE DRAWINGS

FIG. 1 is a perspective view of one embodiment of the present invention.

FIG. 2 is a cross-section view of the present invention taken along line 2—2 of FIG. 1.

FIG. 3 is an cross-section view of the present invention taken along line 3—3 of FIG. 1.

FIG. 4 is a perspective view of a second embodiment of the present invention.

FIG. 5 is a cross-section view of the second embodiment of the present invention taken along line 5—5 of FIG. 4.

FIG. 6 is a top view showing the lid of the second embodiment of the present invention.

DETAILED DESCRIPTION OF THE PREFERRED EMBODIMENT

The present invention consists of a cassette with multiple compartments for temporary storage of orthodontic bands during the sterilization process. As shown in FIG. 1, the cassette 10 is formed in the shape of a box having base 11, endwalls 12, and two substantially parallel sidewalls 13. Dividers 15 are shown in FIG. 2, which is a cross-section view of the cassette. The dividers 15 which separate the container into multiple compartments may be either movable or immovable and they extend generally from the base of the cassette to a point near groove 30, shown in FIG. 3, which is near the top of sidewalls 13. Each of the dividers 15 have edges closely abutting its associated adjacent inner surface of the base, wall and lid, respectively, the edges being sufficiently flat to prevent passage therebetween of an orthodontic band identified for one compartment to an adjacent compartment.

The cassette 10 comprises a lid 14 which slides open to allow access to the interior compartments of the cassette 10. The cassette 10 further comprises a first indicia 16a which identifies each compartment of the cassette 10 with respect to the jaw of the patient's mouth, such as upper (maxillary) or lower (mandibular) and a second indicia 16b which, when taken with the first indicia 16a, identifies each quadrant of a patient's mouth (upper right, upper left, lower right, lower left). A third indicia 17, such as a label, indicates the contents of the cassette. Third indicia 17 is used to identify each cassette if multiple cassettes are used. It is anticipated that multiple cassettes will be used by an orthodontist in the band fitting process.

When used for segregation of orthodontic bands third indicia 17 will indicate the type of tooth the bands are designed for, such as maxillary and mandibular cuspids, maxillary and mandibular 1st bicuspids, maxillary and mandibular 2nd bicuspids, maxillary and mandibular 1st molars, maxillary and mandibular 2nd molars, maxillary and mandibular centrals, and maxillary and mandibular laterals, and the first and second indicia 16a and 16b will further segregate the bands by indicating whether they are for an upper or lower (jaw) right or left (quadrant) tooth. Taken together, the three indicia identify a particular tooth in the patient's mouth with each compartment. Other indicia could of course be used for a different segregation method.

The lid 14 for the cassette 10 consists of a sliding member which slides in a groove 30 which is incorporated into the top of the sidewalls 13, as shown in FIG. 3. This sliding lid 14 could include a lip, such as shown by 31, which acts as a stop when closing the lid by abutting against end wall 12. During normal operation, the left (as seen in FIG. 1) edge of protuberance 32 of finger slot 33 is designed to prevent full removal of the sliding member by abutting against the inside surface of end wall 12 beneath half slot 34 formed therein (FIG. 2) while passing easily through full slots 35, 36, 37 (FIG. 3) formed in the top of dividing wall members 15. The half and full slots are sized to prevent identified bands for one compartment from passing through the slots to another compartment. Lid 14 may be initially inserted over the bottom edge of half slot 34 during installation by the exertion of a slight pressure which will cause a small upward flex in lid 14 allowing protuberance 32 to pop over the top of wall 12 through half slot 34, and thereafter act as an effective stop preventing inadvertent removal of lid 14. The lid 14 is selectively held open or closed by friction with the groove 30 in which it slides. The lid 14 slides in the direction indicated by arrow 3 in FIG. 1 in order to close cassette 10. Lid 14 allows selective access to the interior compartments.

Further if it is desired, the lid 14 could be securely closed with a variety of known methods. One such method would be to incorporate notches (not shown) at predetermined places in the groove 30 in which the lid 14 slides and a spring activated lever (not shown) which engages said notch. The lever could be released by the orthodontist or assistant manually releasing the lever. Other simple type of mechanisms to allow the lid to be releasably secured in an open, partially open or closed position are commonly known.

The cassette 10 is manufactured with a perforated material used for the sidewalls, endwalls, and dividers. The lid and the base may be made out of solid or perforated materials. It is preferable to manufacture the base from a solid material so that bodily fluids or other contaminants on the bands do not pass from the cassette onto a working surface. The perforations are shown as numeral 18. The perforations 18 allow steam to penetrate the cassette 10 if it is used in an autoclave. The perforations also allow for sterilizing liquids to penetrate the cassette 10 to sterilize the small parts, such as the orthodontic bands, placed in the cassette. The perforations are sized so that the small parts, such as, orthodontic bands, placed in cassette 10 cannot pass through the perforations. The perforations are sized to prevent the movement of parts between the multiple compartments of cassette 10.

The cassette 10 can be manufactured from any material that can be repeatedly sterilized and can withstand the stress of being repeatedly used in an autoclave or repeatedly exposed to sterilizing liquids. An acceptable material would be surgical steel.

The cassette is used by the orthodontist during the process of fitting orthodontic bands. Usually during this process the orthodontist works on locating a properly sized band for a specific tooth by trial and error, selecting a certain sized band and attempting to fit it on the tooth. If the band is appropriately sized it is fitted to the tooth. If the band is the wrong size, the band which was attempted is placed in the appropriately labelled compartment of the appropriately labelled cassette. The cassette indicating the appropriate indicia for the specific tooth being worked on by the orthodontist would be placed in close proximity to the orthodontist. The cassette 10 would be placed on a counter or other flat surface near the orthodontist. The flat base 11 would be placed on the flat surface. In this orientation the lid 14 would be on the top of the cassette. The lid 14 slides open to allow the attempted bands to be placed in the corresponding marked compartment in the cassette. In this way the bands are segregated to allow for ease of sorting after sterilization. It is common after sterilization to return the bands to the original manufacturers containers.

A second embodiment of the invention is shown in FIGS. 4 and 5. In this embodiment, the cassette 20 is constructed in a manner similar to the cassette 10, except that this cassette does not have a sealed base member. Rather this cassette 20 incorporates two slidable lids 24 on opposite side of the cassette 20. In addition to the vertical dividers 25, the cassette 20 also comprises a horizontal divider 21 which perpendicularly intersects with each of vertical dividers 25 and also separates the cassette into a lower and an upper portion. Preferably, dividers 21 and 25 are perpendicularly intersecting and interlocking by having half slits (not shown) cut into each divider which are mutually engaged. This further division provides cassette 20 with twice as many compartments as cassette 10. All of the edges of horizontal divider 21 closely abut the adjacent inner surface portions of adjoining closure members, respectively, to prevent movement of bands identified for one compartment to an adjacent compartment during the sterilization process.

The cassette is manufactured in dimensions to allow it to be easily used with commonly available sterilization methods, such as placed in an autoclave, a dental ultrasonic sterilizing unit, or cold sterile containers. The cassette is further sized to allow use in those devices while allowing room for the sterilization of other dental instruments.

The cassette is further manufactured so that multiple cassettes can be placed together in a single case thereby reducing the storage room necessary for the cassettes.

While the invention has been described with reference to the preferred embodiments thereof, those skilled in the art will understand that variations in design, detail, size, shape and choice of materials for manufacture may be made and still fall within the spirit and scope of the present invention, which is intended to be limited only by the claims appended hereto.

I claim:

1. A sterilization cassette comprising:
two generally parallel sidewalls and two generally parallel endwalls generally perpendicular to said sidewalls, the sidewalls and endwalls attached to a base also generally perpendicular to said sidewalls, said sidewalls, endwalls and base defining a generally rectangular container having an upper opening adjacent an upper edge of the sidewalls and endwalls;
a plurality of dividing wall members supported in the container, each of said plurality of wall members having end, top and bottom edges, thereby defining a plurality of discrete compartments within said generally rectangular container;
a generally flat lid portion operably associated with said upper edge of said side or end walls to releaseably close said upper opening;
a first indicia disposed on each of said compartments identifying a jaw of a patient's mouth;
a second indicia disposed on each of said compartments identifying a quadrant of a patient's mouth;
a third indicia disposed on said container or lid identifying each of said discrete compartments with an associated orthodontic band for a tooth,
a plurality of openings in the container or lid for admitting a sterilization liquid to each compartment for sterilizing orthodontic bands placed therein, and
each of said edges closely abutting its associated adjacent inner surface of said base, wall and lid, respectively and being sufficiently flat to prevent passage therebetween of an orthodontic band identified for one compartment to an adjacent compartment.

2. The cassette of claim 1 wherein the base, sidewalls, endwalls lid and dividing walls are metal.

3. The cassette of claim 1 further comprising a plurality of openings in at least one of said sidewalls, said endwalls, said base, said lid, and said dividing wall members.

4. The cassette of claim 1, wherein the cassette is made from autoclavable material.

5. The cassette of claim 3 wherein the autoclavable material further comprises surgical steel.

6. The cassette of claim 1 where the dividing wall members are positioned substantially parallel to the endwalls.

7. A sterilization cassette comprising:
generally parallel and vertical sidewalls and a pair of generally vertical endwalls attached by a horizontal base, each of said sidewalls having an inner groove in close proximity to an upper longitudinal edge thereof, said sidewalls, endwalls and base defining a generally rectangular container;
a plurality of dividing wall members, each of said plurality of dividing wall members having end, top and bottom edges, and being supported in the container, thereby defining a plurality of discrete compartments within said generally rectangular container;
a generally flat lid portion engaging said inner groove in each of said sidewalls and being reciprocally moveable in said grooves;
multiple indicia disposed on said rectangular container identifying each compartment with respect to an orthodontic band associated with a tooth located in a particular section of a patient's mouth;
a plurality of openings in the container or lid for admitting a sterilization liquid to each compartment for sterilizing orthodontic bands placed therein;
each of said edges closely abutting its associated adjacent inner surface of said base, wall and lid, respectively and being sufficiently flat to prevent passage therebetween of an orthodontic band identified for one compartment to an adjacent compartment; and
the lid being reciprocable without interference with the top edges of the dividing wall members or contents of the compartments.

8. The cassette of claim 7 wherein the base, sidewalls, endwalls, lid and dividing walls are metal.

9. The cassette of claim 7 further comprising a plurality of openings in at least one of said sidewalls, said endwalls, said base, said lid, and said dividing wall members.

10. The cassette of claim 7, wherein the cassette is made from autoclavable material.

11. The cassette of claim 1 0 wherein the autoclavable material further comprises surgical steel.

12. The cassette of claim 7 where the dividing wall members are positioned substantially parallel to the endwalls.

13. A sterilization cassette comprising:
two generally parallel and vertical sidewalls attached by a pair of generally vertical endwalls forming the side and end walls of a container with openings at the top and bottom thereof;
a plurality of vertical dividing wall members generally parallel to the end wall members and generally perpendicularly intersecting with a horizontal longitudinal dividing wall member which is generally perpendicular to the sidewall and endwall members, thereby defining a plurality of discrete interior compartments in the container;
the vertical dividing wall members having top, bottom and side edges and the longitudinal dividing wall member having end and side edges;
at least one flat lid member releaseably attached to the container and enclosing each of said openings;
a first indicia disposed on each of said compartments identifying a jaw of a patient's mouth;
a second indicia disposed on each of said compartments identifying a quadrant of a patient's mouth;
a third indicia disposed on said container or one or more lids identifying each of said discrete compartments with an associated orthodontic band for a tooth;
a plurality of openings in the container or lids for admitting a sterilization liquid to each compartment for sterilizing orthodontic bands placed therein; and
each of said edges closely abutting its associated adjacent inner surface of said wall and lid member, respectively, and being sufficiently flat to prevent passage therebetween of an orthodontic band identified for one compartment to an adjacent compartment.

14. The cassette of claim 13 wherein the base, sidewalls, endwalls, lid and dividing walls are metal.

15. The cassette of claim 13 further comprising a plurality of openings in at least one of said sidewalls, said endwalls, said base, and said dividing wall members.

16. The cassette of claim 13, wherein the cassette is made from autoclavable material.

17. The cassette of claim 16 wherein the autoclavable material further comprises surgical steel.

18. A sterilization cassette for orthodontic bands for teeth in a patient's mouth comprising:
a rectangular-shaped container having a base attached to a pair of flat, generally parallel, transverse, upstanding closure members and a pair of flat, generally parallel, longitudinal, upstanding closure members and at least one open side;
a plurality of dividers generally parallel to the transverse closure members and generally perpendicularly intersecting with at least one longitudinal divider generally parallel to the longitudinal closure members and supported in the container whereby the container is divided into a plurality of discrete compartments adapted for housing in each compartment a plurality of sizes of orthodontic bands for one tooth from among a plurality of orthodontic bands of different sizes of different teeth;
first indicia on each compartment identifying the patient's jaw to which the bands for that compartment relate;
second indicia on each compartment identifying the patient's mouth quadrant to which the bands for that compartment relate;
at least one lid having a flat surface portion, being releaseably attached to the container and closing the at least one open side of the container;
third indicia on the container or lid identifying each of the compartments of the container that relate to a type of tooth; and
a plurality of perforations in the container or lid smaller than the smallest band for admitting a sterilization fluid into each of the discrete compartments;
whereby all compartments may be accessed through the at least one open face of the container and non-sterile bands placed and retained therein for sterilization without loss or intermixing of bands among compartments.

19. The sterilization cassette of claim 18 further comprising:
the dividers having bottom, top and end edges each of which closely abuts its associated adjacent inner surface of the base, closure member and lid, respectively, and is sufficiently flat to prevent passage therebetween of an orthodontic band identified for one compartment to an adjacent compartment.

20. The sterilization cassette of claim 19 wherein the container, dividers and lid are metal.

* * * * *